US005886534A

United States Patent [19]

Bakhtiari et al.

[11] Patent Number: 5,886,534

[45] Date of Patent: Mar. 23, 1999

[54] MILLIMETER WAVE SENSOR FOR ON-LINE INSPECTION OF THIN SHEET DIELECTRICS

[75] Inventors: Sasan Bakhtiari, Westmont; Nachappa Gopalsami, Naperville; Apostolos C. Raptis, Downers Grove, all of Ill.

[73] Assignee: The University of Chicago, Chicago, Ill.

[21] Appl. No.: 927,363

[22] Filed: Sep. 9, 1997

Related U.S. Application Data

[63] Continuation-in-part of Ser. No. 549,454, Oct. 27, 1995, abandoned.

[51] Int. Cl.[6] .............................. G01N 22/02; G01R 27/04

[52] U.S. Cl. .............................. 324/642; 324/646; 324/644

[58] Field of Search .............................. 324/637, 638, 324/642, 643, 644, 646

[56] References Cited

U.S. PATENT DOCUMENTS

| | | | |
|---|---|---|---|
| 4,075,555 | 2/1978 | Wright et al. | 324/644 |
| 4,344,030 | 8/1982 | Anderson et al. | 324/642 |
| 4,704,576 | 11/1987 | Tributsch et al. | 324/642 |
| 4,839,588 | 6/1989 | Jantsch et al. | 324/642 |
| 4,949,034 | 8/1990 | Imura et al. | 324/642 |
| 5,438,276 | 8/1995 | Kawata et al. | 324/642 |
| 5,502,394 | 3/1996 | Piau | 324/646 |
| 5,600,253 | 2/1997 | Cohen et al. | 324/644 |

OTHER PUBLICATIONS

"Millimeter Wave Imaging for Nondestructive Evaluation of Materials" *Materials Evaluation*, vol. 52, No. 3, Mar., 1994, pp. 412–415, by N. Gopalsami, S. Bakhtiari, S. L. Dieckman, A.C. Raptis and M. J. Lepper.

*Primary Examiner*—Diep N. Do
*Attorney, Agent, or Firm*—Mason, Kolehmainen, Rathburn & Wyss

[57] ABSTRACT

A millimeter wave sensor is provided for non-destructive inspection of thin sheet dielectric materials. The millimeter wave sensor includes a Gunn diode oscillator (GDO) source generating a mill meter wave electromagnetic energy signal having a single frequency. A heater is coupled to the GDO source for stabilizing the single frequency. A small size antenna is coupled to the GDO source for transmitting the millimeter wave electromagnetic energy signal to a sample material and for receiving a reflected millimeter wave electromagnetic energy signal from the sample material. Ferrite circulator isolators coupled between the GDO source and the antenna separate the millimeter wave electromagnetic energy signal into transmitted and received electromagnetic energy signal components and a detector detects change in both amplitude and phase of the transmitted and received electromagnetic energy signal components.

14 Claims, 12 Drawing Sheets

MILLIMETER WAVE SENSOR FOR ON-LINE INSPECTION OF THIN SHEET DIELECTRICS

This is a continuation-in-part of U.S. patent application Ser. No. 08/549,454 filed Oct. 27, 1995, abandoned.

CONTRACTUAL ORIGIN OF THE INVENTION

The United States Government has rights in this invention pursuant to Contract No. W-31-109-ENG-38 between the United States Government and Argonne National Laboratory.

BACKGROUND OF THE INVENTION

1. Field of the Invention

This invention relates to a millimeter wave sensor operating primarily on a single frequency to provide online inspection, preferably including continuous monitoring, of thin sheet dielectric materials, such as fabric, paper, plastic and other dielectric products with respect to macroscopic and/or microscopic properties such as density, homogeneity, for example internal flaws, structure, porosity, moisture content, and state of cure. More particularly, the invention relates to a sensor and instrument system operating primarily on a single frequency within the range of about 75–110 GHz with the frequency selected on the characteristics of the sample to provide greater resolution, sensitivity and other data important for the inspection. Of particular importance is the measurement of the amplitude and phase characteristics of the reflected/transmitted signal as a result of variations in properties of the material medium.

2. Description of the Prior Art

The use of microwaves for nondestructive evaluation (NDE) of materials is gaining importance due to the inherently noncontact nature of the technique, good depth of penetration in low-loss dielectric materials, and the emergence of new and advanced materials that pose new NDE challenges that require new solutions. The material property that is sensed by microwave techniques is the change in dielectric properties, such as permittivity and loss factor.

"MILLIMETER WAVE IMAGING FOR NONDESTRUCTIVE EVALUATION OF MATERIALS", *Material Evaluation*, Volume 52, Number 3, March, 1994 Pps. 412–415, by Nachappa Gopalsami, Sasan Bakhtiari, Stephen L. Dieckman, Apostolos C. Raptis, and Matthew J. Lepper, describes a millimeter-wave imaging system in the W band (75–110 GHz) for nondestructive evaluation of low-loss materials. The subject matter of the above-identified publication is incorporated herein by reference. A theoretical analysis of the millimeter-wave imaging is provided.

A W-band imaging system was initially developed for high resolution inspection of electrically thick samples of stratified dielectric slabs. The system operated either in a bistatic forward-scatter configuration with separate antennas to transmit and receive or a monostatic backscatter configuration with a single antenna used both to transmit and receive. The system offered minimal diffraction loss due to incorporation of Gaussian optic lens antennas. The antenna lenses had an aperture diameter D=12" and a focal length f=12" (i.e., f/D=1). The spot size of the beam at the focal point was about one wavelength (3-dB beamwidth) and had a depth of focus of about $10\lambda$. The backward-wave oscillator (BWO) source output frequency was stabilized using a source-locking frequency counter. A sample to be tested was mounted in a plane perpendicular to the incident beam axis within the focal depth of the antenna. In the monostatic case, a circulator or a hybrid coupler separated the transmitted and reflected waves. Only the amplitude of the scattered fields or the received power was measured with this apparatus. The output detected via a diode detector was amplified, digitized, and acquired by a personal computer. The computer also controlled a two-axis translation stage for scanning the sample.

A principal object of the present invention is to provide an improved millimeter wave(MMW) sensor for on-line inspection of thin sheet dielectrics.

It is another object of the present invention to provide such an improved millimeter wave (MMW) sensor for on-line inspection of thin sheet dielectrics that operates primarily on a single frequency within the range of about 75 GHz to 110 Ghz, that is compact and has a small size antenna, and that is self calibrating.

It is another object of the present invention to provide such an improved millimeter wave (MMW) sensor for on-line inspection of thin sheet dielectrics that operates primarily on a single frequency within the range of about 75 GHz to 110 GHz with the single frequency selected on the basis of characteristics of a particular sample to provide greater resolution, sensitivity and other data important for the inspection.

It is another object of the present invention to provide such an improved millimeter wave sensor for on-line inspection of thin sheet dielectrics that measures both the amplitude and phase characteristics of the reflected/transmitted signal as a result of variations in properties of the material medium.

It is another object of the present invention to provide such an improved millimeter wave sensor for on-line inspection of thin sheet dielectrics that overcomes many of the disadvantages of prior art arrangements.

SUMMARY OF THE INVENTION

In brief, these and other objects and advantages of the invention are provided by an improved millimeter wave sensor for non-destructive inspection of thin sheet dielectric materials. The millimeter wave sensor includes a Gunn diode oscillator (GDO) source generating a millimeter wave electromagnetic energy signal having a single frequency. A heater is coupled to the GDO source for stabilizing the singe frequency. A small size antenna is coupled to the GDO source for transmitting the millimeter wave electromagnetic energy signal to a sample material and for receiving a reflected millimeter wave electromagnetic energy signal from the sample material. Ferrite circulator and isolators coupled between the GDO source and the antenna separate the millimeter wave electromagnetic energy signal into transmitted and received electromagnetic energy signal components and a detector detects change in both amplitude and phase of the transmitted and received electromagnetic energy signal components.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

Figure 1A:
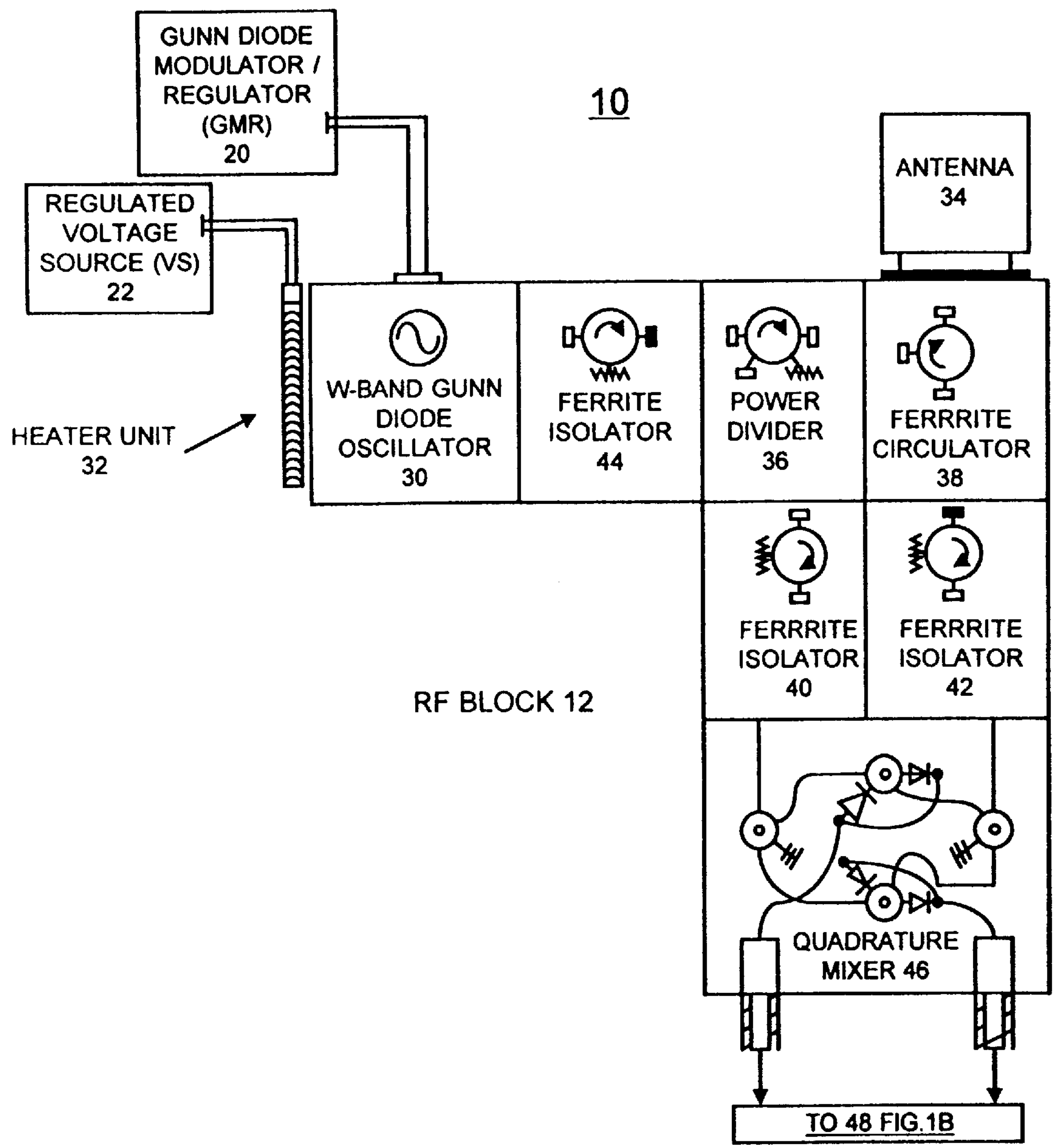
FIG. 1A is a schematic and block diagram representation of a millimeter wave sensor for on-line inspection of thin sheet dielectrics of a millimeter wave system in accordance with the present invention.
Figure 1B:
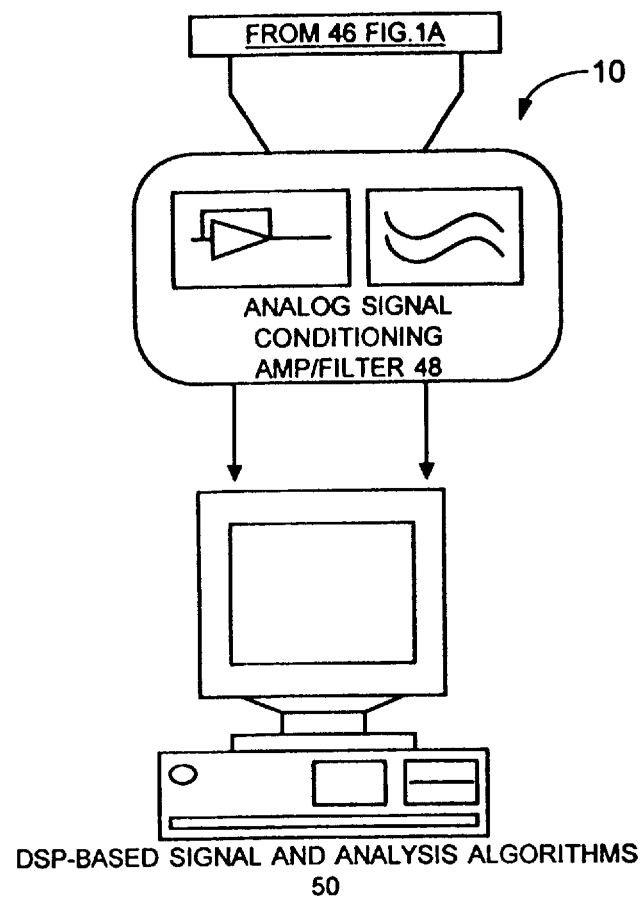
FIG. 1B is a schematic and block diagram of an analog signal conditioning and digital signal processing (DSP) signal detection and analysis function used with the millimeter wave sensor of FIG. lA in the millimeter wave system in accordance with the present invention.
Figure 1C:
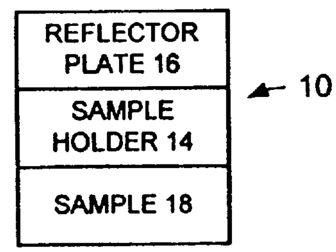
FIG. 1C is a schematic and block diagram of a sample, holder and reflector plate used with the millimeter wave sensor of FIG. 1A in the millimeter wave system in accordance with the present invention

Having reference now to the drawings, in FIGS. 1A, 1B and 1C, there is shown a millimeter wave (MMW) system for continuous monitoring of low-loss, thin sheet dielectric materials generally designated by the reference character 10. Typical applications for the MMW system 10 include continuous monitoring of low-loss dielectric sheet material production, such as, for quality control in fabric, paper, and plastic industries. With proper calibration, the MMW system 10 can be utilized for measurement of material property as well as dimensional variations.

The term microwaves designate the electromagnetic (EM) frequency spectrum occupying the range between 3 MHz and 300,000 MHz (300 GHz). The upper decade of this band with wavelengths below 1 centimeter is referred to as millimeter wave (MMW) region. Penetration of microwave energy inside dielectric media and its sensitivity of minute changes in material medium coupled with availability of relatively large bandwidths are of great significance for nondestructive evaluation (NDE) applications of MMW system 10. Both macroscopic and microscopic properties such as density, homogeneity, for example, internal flaws, structure, porosity, moisture content, state of cure, and molecular structure have been examined in materials in solid, liquid and gaseous phase. Interaction of EM field with the medium in general takes place either with conduction electrons or with molecular dipoles resulting in attenuation and phase variation of the traveling wave. The electrical properties of non-magnetic material media can be described in terms of the constitutive parameter $\epsilon_r=\epsilon'_r-j\epsilon''_r$, referred to as the relative complex dielectric constant. This quantity once measured based on the change in the through transmitted or reflected radiation, can provide accurate information about the electrical properties of the medium and subsequently be related to various material characteristics. Furthermore, polarization dependency of a coherent electromagnetic wave can provide information about orientation related properties, for example, orientation of internal flaws or fiber reinforcements in composites.

Referring now to FIG. 1A, system 10 includes a millimeter wave sensor generally designated by the reference character 12 arranged for on-line inspection of thin sheet dielectrics. Microwave reflection sensor 12 is used to measure the complex reflection coefficient which is calculated through measurement of the change in the amplitude and phase of the reflected signal as a result of variations in properties of a sample 18 or the material medium under test, illustrated in FIG. 1C. The forward transmitted microwave signal which undergoes reflections, refraction, attenuation and polarization changes, upon reception renders information about the state of material in an on-line, real-time basis. Calibrated measurements may be made either at multiple frequencies or at a single frequency if an estimate of the thickness is available. In either case knowledge of the complex dielectric properties of the medium under test and its conceivable variations as a function of frequency and environmental factors, for example temperature, moisture, and the like, are of vital importance.

As shown in FIG. 1C, a reflector plate 16 is positioned behind a sample holder 14 that supports the dielectric sample 18 being monitored. A compact arrangement of the source and transmit/receive components or RF block forming MMW sensor 12 is provided. Sensor 12 includes a small, low-power solid-state Gunn-diode oscillator (GDO) source 30 which generates millimeter wave electromagnetic energy. MMW sensor 12 includes a heater unit 32 coupled to the GDO 30 which stabilizes the frequency of the Gunn diode oscillator source. A single antenna 34 transmits and receives millimeter wave electromagnetic energy to and from the sample 18. A power driver 36 drives the millimeter wave radiation into two components; one for transmission as the RF signal and one as the LO signal. A plurality of ferrite circulators 38, 40, 42 and 44 allows for coupling of energy between adjacent ports in a clockwise manner, resulting in separation of transmitted and received energy. A MMW quadrature mixer 46 combines the RF and LO signals and produces two quadrature output voltage signals labeled IF1 and IF2. Modular antenna 34 may consist of any standard millimeter wave antenna which would best fit the sensing application.

Important features of the invention include the incorporation of the bias-tuned GDO 30 as the MMW source together with a heater unit 32 coupled to the GDO for frequency stabilization. Other important features include the incorporation of an appropriate small size antenna 34 and the MMW quadrature mixer 46, and the utilization of block-type and microstrip components forming sensor 12. Due to physical size limitations for incorporation of phase-locking circuitry, as well as cost considerations, the biased tuned GDO 30 is mounted on the compact heater unit 32 providing for both fast stabilization of the source and minimization of frequency drift.

Commercially available components that can be used for the MMW components 30, 32, 34, 36, 38, 40, 42 and 44 are manufactured and sold by various suppliers including ALPHA Industries, Inc., Methuen, Mass. 01844; AEROWAVE Inc., Medford, Mass. 02155; EPSILON LAMBDA Electronics, Geneva, Ill. 60134; M/A COM Millimeter Wave Products, INC., Burlington, Mass. 01803; MILLITECH Corporation, South Deerfield, Mass. 01373.

The components outside the RF block 12 consist of two power supplies including a Gunn modulator regulator (GMR) supply 20 coupled to the GDO 30 and a voltage source 22 (VR) coupled to the heater unit 32, a signal conditioning amplifier and filter block 48 and a data acquisition and display unit represented by a computer 50.

Operation of the RF block or MMW sensor 12 may be understood as follows. A continuous wave (CW) signal at a selected frequency from the GDO 30, which is operated with a small DC bias via the modulator regulator 20, is separated into transmitted and received components. The power divider 36 used for this task is a matched hybrid ring which advantageously is constructed directly on a printed circuit board (not shown) supporting sensor 12. The RF signal is then fed to the antenna 34 via the ferrite circulator 38. The returned signal couples back in to the RF arm via the circulator 42. MMW ferrite circulators 38, 40, 42 and 44 in general provide for 30 dB isolation between the transmitted and received signals with minimal insertion loss. Ferrite circulator isolators 40 and 42 incorporated in the RF and LO arms reduce unwanted reflections otherwise causing standing waves within the system 10. The two arms are then fed as the inputs to the quadrature mixer (QIFM) 46 which ultimately provides for the in-phase and quadrature signal components. The outputs IF1, IF2 from the detector 46 are amplified, filtered at block 48 and subsequently digitized by a digital signal processing (DSP) board (not shown) integrated within the computer 50.

The millimeter wave (MMW) sensor 12 is arranged for application to on-line or off-line inspection of thin sheet dielectric materials. Some typical applications may include continuous monitoring of low-loss dielectric sheet materials such as for quality control in paper, plastic, and ceramic industries. With proper calibration, the device can be utilized for measurement of material property as well as dimensional variations. Both macroscopic and microscopic properties can be examined. With ever increasing use of strong, lightweight, and heat resistant advanced ceramics, plastics, and various fiber reinforced dielectric composites in industrial and scientific applications, there is a growing demand for real-time, in situ , and practical NDE of such materials. Millimeter-wave sensor 12 is well suited for nondestructive inspection of such low-loss dielectric materials. In many practical on-line or off-line NDE arrangements access to both sides of the material under test is either difficult or is strictly limited to one side. For example, one application for MMW sensor 12 is the examination of coatings disposed on a conducting surface.

Figure 2A:
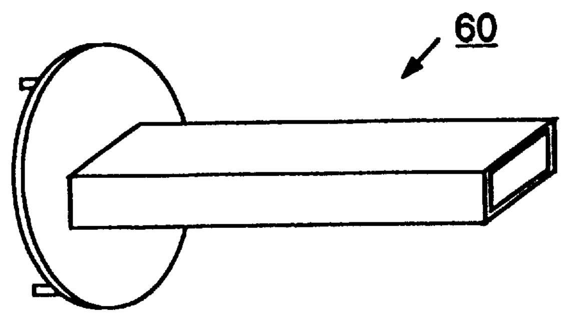
FIGS. 2A, 2B and 2C are schematic diagram representation of alternative antennas for use in the millimeter wave sensor for on-line inspection of thin sheet dielectrics of FIG. 1.
Figure 2B:
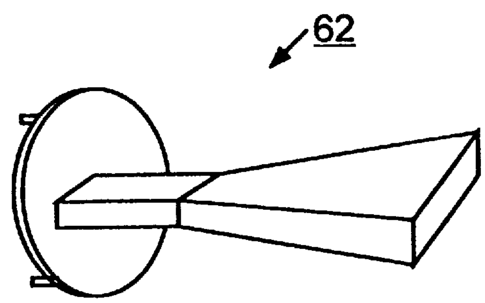
Figure 2C:
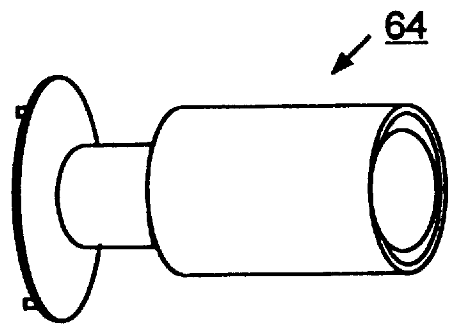

Referring FIGS. 2A, 2B and 2C, a respective alternative types of antennas 60, 62 and 64 is shown for use in sensor 12. One of the major challenges in making the stationary system 10 useful for on-line application is the incorporation of an appropriate antenna type, such as 60, 62 and 64 for the antenna 34 for various close proximity sensing applications. One of a wide array of millimeter wave antennas is selected as best suited for specific applications. Analogous to their low-frequency microwave counterparts, the antenna 3 dB beamwidth ($\theta_3$dB) and far-field radius ($R_{FF}$) can be estimated in general as:

$$\theta_{3dB}=70(\lambda/D)(\text{degrees}) \quad (1)$$

$$R_{FF}=(2D^2/\lambda) \quad (2)$$

where $\lambda$ is the operating wavelength and D is the largest dimension of the antenna. The above simplified equations indicate that at short MMW wavelengths antennas used for antenna 34 can be constructed in a compact size with a short far-field radius. Due to wide range of applications intended for the MMW sensor 12, it was designed as a modular unit which allows for the antenna 34 to be easily exchanged. Different antenna probes such as open-ended waveguide 60, standard gain pyramidal horn 62, and corrugated scalar horn 64, respectively depicted in FIG. 2A, 2B, and 2C, have been tested on system 10. Each antenna 60, 62, and 64, having a different radiation pattern, offers specific characteristics suited for different applications. Aside from symmetry of the radiation patterns for individual antennas 60, 62, and 64, as can be seen from the above equations (1) and (2), the tradeoffs are between size of antenna footprint and far-field distance. In general, smaller aperture antennas, operating very near the surface of the test material, offer better resolutions. On the other hand, for applications demanding volume effect sensing, such as most material property measurement applications, larger diameter antennas such as standard gain horn 62 are better suited.

Measurement of the reflected radiation is made by placing the sample 18 within the focal depth of the antenna 34. MMW sensor 12 enables measurement of both the amplitude and phase of the reflected radiation. For the reflection setup, the signal is separated into transmitted and received components with a matched hybrid coupler 36 and the conducting plate 16 is placed behind a sample 18 within the focal depth of the antenna. A single frequency within the 75–100 GHz is selected for GDO 30 based on the characteristics of the dielectric sample 18. It is important to measure both amplitude and phase to distinguish between different properties of the material 18 and defects, such as oil and water, and to provide improved imaging. The quadrature IF mixer (QIFM) 46 is utilized to measure both the relative amplitude and phase variations of the reflected or through-transmitted radiation. The two outputs IF1 and IF2 of the mixer 46 are DC signals proportional to in-phase and quadrature components of the difference signal between the RF and LO ports. Outputs IF1 and IF2 from the mixer are amplified and filtered with the balanced amplifier 48 which facilitates large DC offset adjustment and amplification of the received signal, therefore greatly enhancing sensitivity and dynamic range.

Figure 2D:
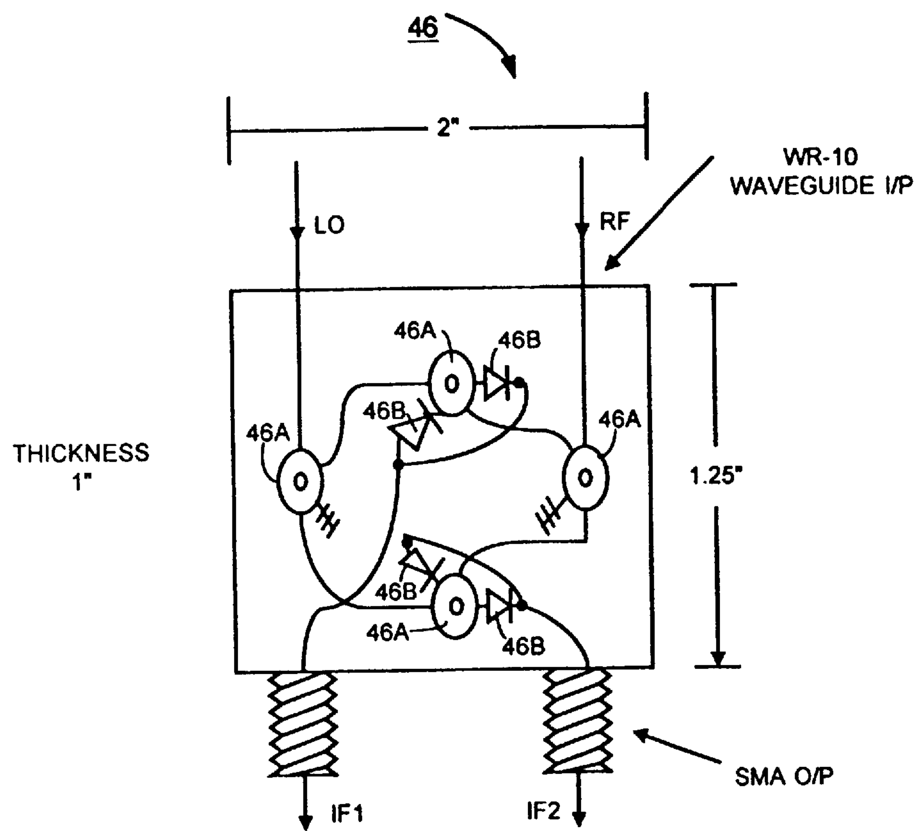
FIG. 2D is a schematic diagram representation of a quadrature mixer used in the millimeter wave sensor for on-line inspection of thin sheet dielectrics of FIG. 1A.
Figure 3:
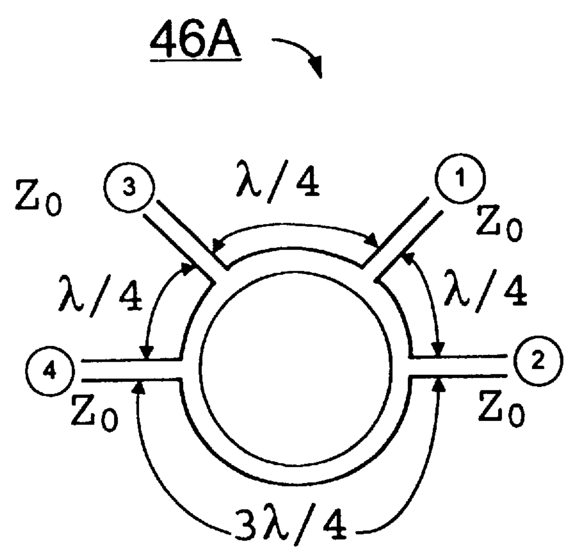
FIG. 3 is a schematic diagram representation illustrating a single microstrip line hybrid ring (rat-race) used in the quadrature mixer of FIGS. 1A and 2.

Referring to FIGS. 2D and 3, FIG. 2D depicts an isolated drawing of the quadrature mixer section block 46 of the MMW sensor 12 of FIG. 1A. FIG. 3 illustrates the basic operation of a single hybrid junction (rat race) 46A. As shown in FIGS. 1A and 2, the inputs to the MMW quadrature mixer 46 are the LO signal or reference transmitted signal, and the RF signal or the reflection from test specimen signal, which are combined in a particular manner to provide in-phase and quadrature components of the signal that is modulated by the test specimen. The MMW quadrature mixer 46 consists of eight major components 46A and 46B, namely, four passive microstrip hybrid rings (rat-race) 46A and four active solid-state mixer diodes 46B. The active components are surface oriented beam-lead GaAs millimeter wave schottky barrier junctions. The photolithographically constructed hybrid rings 40A are configured such that they act as in-phase and quadrature power dividers and also as combiners for balanced mixing circuitry. Realization of QIFM at millimeter wave frequencies using microstrip line technology poses particular challenges which is described below.

Referring to FIG. 3, millimeter wave signal $Z_O$ incident at port 1 will divide into two components which arrive in phase (equal path-lengths $\lambda/4$) at ports 2 and 3, and 180° out of phase at port 4. Similarly, the wave signal $Z_0$ incident at port 4 will arrive in phase at ports 2 and 3 and with a net phase difference of 180° at port 1. Alternatively, ports 1 and 4 can be considered as sum and difference ports when two millimeter wave signals $Z_0$ of the same frequency are incident on ports 2 and 3. Therefore a single element microstrip line hybrid ring 46A can be utilized either as a power divider or combiner depending on excitation of different ports. The quadrature mixer section block 46 shown in FIG. 2D utilizes a combination of four matched hybrid rings 46A, with two hybrid rings 46A acting as power dividers, and two hybrid rings 46A functioning as power combiners that are mounted respectively with one of two sets of matched diodes 46B that act as nonlinear mixing elements.

The basic operation of the millimeter wave microstrip line quadrature mixer 46 involves in-phase splitting of LO signal and quadrature splitting of RF signal which are then mixed via the remaining two hybrid junctions 46A that are mounted with two opposite polarity matched detector diode elements 46B, as shown in FIG. 2. A sinusoidal signals LO and RF with radial frequencies $\omega_{LO}$ and $\omega_{RF}$ are combined in phase through the first balanced mixing stage and 90° out of phase through the second balance mixing stage. At the mixer outputs these signals would appear as:

$$\cos(\omega_{LO}t)\cos(\omega_{RF}t)=0.5(\cos((\omega_{LO}+\omega_{RF})t+\cos(\omega_{LO}-\omega_{RF})t) \quad (1)$$

$$\cos(\omega_{LO}t)\sin(\omega_{RF}t)=0.5(\sin((\omega_{LO}+\omega_{RF})t+\sin(\omega_{LO}-\omega_{RF})t) \quad (2)$$

subsequent to lowpass filtering, the first order approximation for difference frequency (mixed IF output signals) can then be written as the second term in the above equations (1) and (2) as $$S_{IF1}\propto A\cos((\omega_{LO}-\omega_{RF})t+\phi) \quad (3)$$

$$S_{IF2}\propto A\sin((\omega_{LO}-\omega_{RF})t+\phi) \quad (4)$$

where A and $\phi$ denote amplitude and phase variations due to modulation of the reflected signal by the test specimen when LO output power is kept constant. In reference to the above equations (3) and (4), when these two frequencies are equal, the mixer IF outputs IF1 and IF2 are DC signals proportional to in-phase and quadrature components of the RF input. With proper bias and matching circuitry, this configuration improves both the isolation between LO and RF ports and also allows for cancellation of AM noise from the local oscillator 30 in FIG. 1A.

Figure 4:
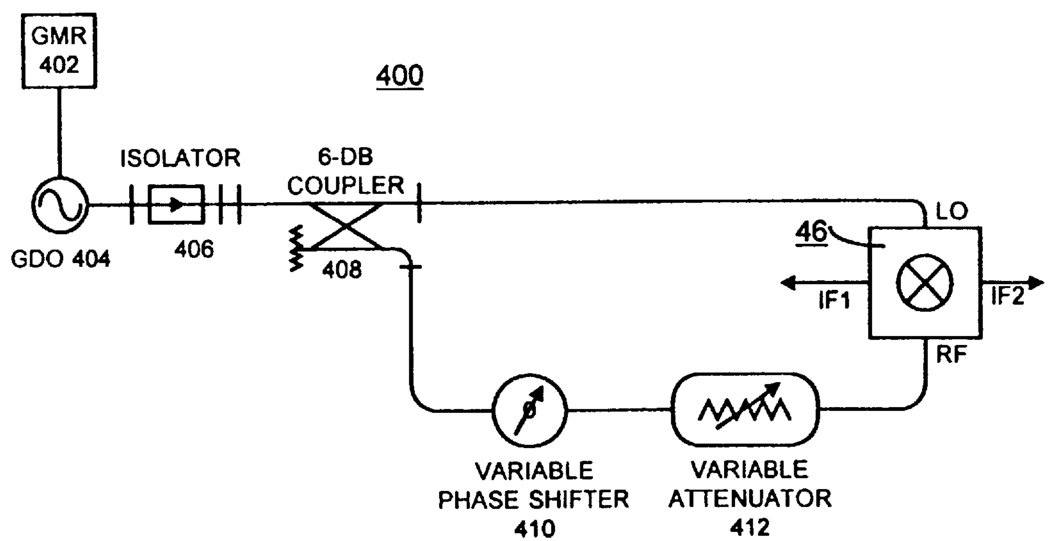
FIG. 4 is a schematic diagram representation illustrating a phase measurement setup for determining characteristics of the quadrature mixer of FIGS. 1A and 2.

FIG. 4 illustrates a test apparatus 400 used to determine characteristics of the quadrature mixer 46 prior to integration into the sensor block 12. Test apparatus 400 includes a Gunn modulator regulator (GMR) supply 40 coupled to a Gunn diode oscillator (GDO) 404, an isolator 406, a 6-dB waveguide directional coupler 408. To examine the quadrature phase dependence of the mixer IF1 and IF2 outputs, a 94 GHz signal from a MMW source 402 was divided into LO and RF components via a 6-dB waveguide directional coupler. Test apparatus 400 includes a calibrated variable phase shifter 410 and a variable attenuator 412 inserted in the RF arm input to quadrature mixer 46 both to account for input power difference between the RF and LO ports as well as to allow for precise adjustment of RF phase.

Realization of the quadrature mixer 46 described above using microstrip line technology poses particular engineering challenges at millimeter wave frequencies. The difficulties are primarily due to quadrature phase tuning, matching and balancing of diodes, and proper packaging of the device. Unlike microwave components operating in wavelengths that are one to two order of magnitude larger, proper phase matching and tuning of millimeter wave components are formidable engineering challenges at millimeter wavelengths using microstrip line technology. For minimal conversion and insertion loss, all phase tuning and matching is carried out with extreme efficiency (i.e., shortest path lengths for minimal attenuation) and accuracy (i.e., larger phase variation at shorter wavelength). Overlapped microstrip line technology was incorporated for phase tuning and matching of the quadrature mixer. Unlike conventional microstrip transmission line printed circuitry in which the top planar layer structure is terminated into air, the overlapped microstrip technique utilizes a dielectric slab layer as the top layer for proper phase matching over a shorter path-lengths. The dielectric top layer having a relative permittivity greater than one (free-space has relative dielectric constant $\epsilon_{rO}=1+j_O$) the insertion of dielectric slab layer results in an effective path-length of:

$$\lambda_d=\lambda_0/\sqrt{\epsilon_{rd}} \quad (5)$$

where $\lambda_0$ denotes free-space wavelength and $\lambda_d$ wavelength inside the dielectric layer with permittivity $\epsilon_{rd}(>1)$. Precise matching and tuning is required both for accurate quadrature phase shift as well as proper balance for amplitude measurements. This is of critical importance due to the fact that software-based calibrations are limited in terms of compensating for possible quadrature signal imbalances.

Figure 5:
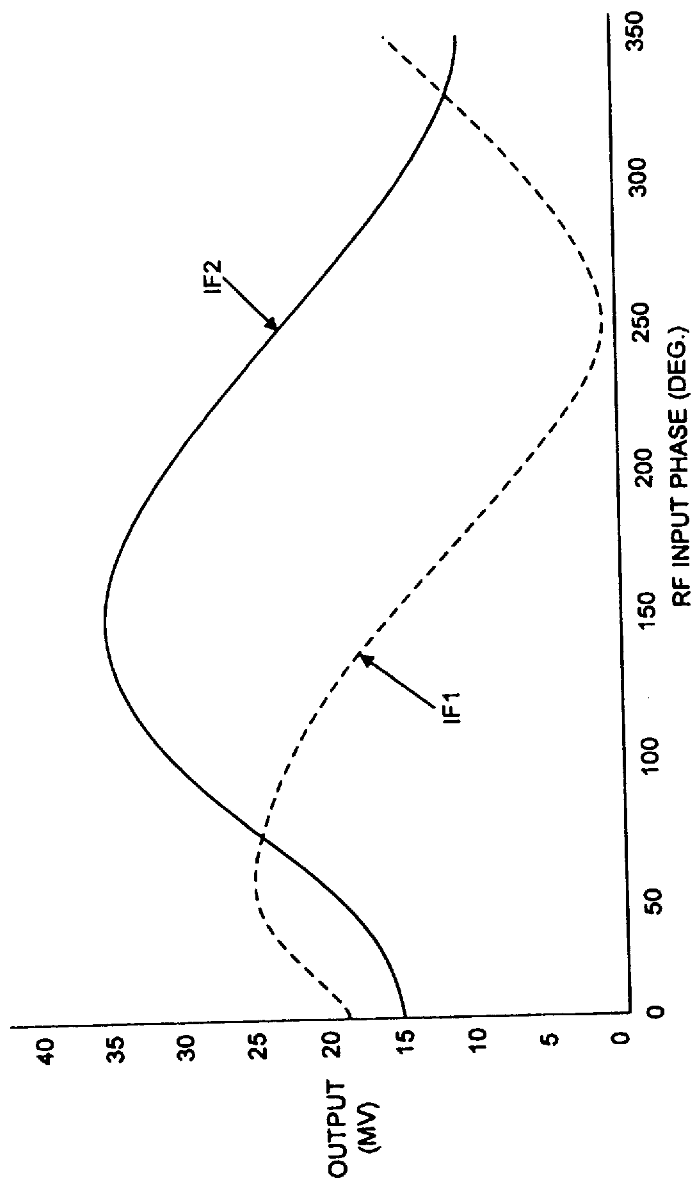
FIG. 5 is a graph illustrating along the vertical axis DC outputs, IF1 and IF2 of the quadrature mixer of FIGS. 1A and 2, with respect to incremental change in RF input phase along the horizontal axis for the quadrature mixer phase measurement setup of FIG. 5.

FIG. 5 provides a plot of the DC outputs IF1, IF2 of the quadrature mixer 46 as function of change in RF phase that was measured in 10° increments covering more than one operating wavelength. Comparison of phase difference between two voltage maxima (or minima) in FIG. 5 indicates a 90° phase separation between IF1 and IF2 output channels. Normalization and calibration of the two phase quadrature DC outputs allows for accurate amplitude and phase measurement. The software based calibration/normalization implemented in the inspection system 10 further allows for DC offset adjustment as well as compensation for any small imbalances between the two output ports IF1, IF2.

Figure 6:
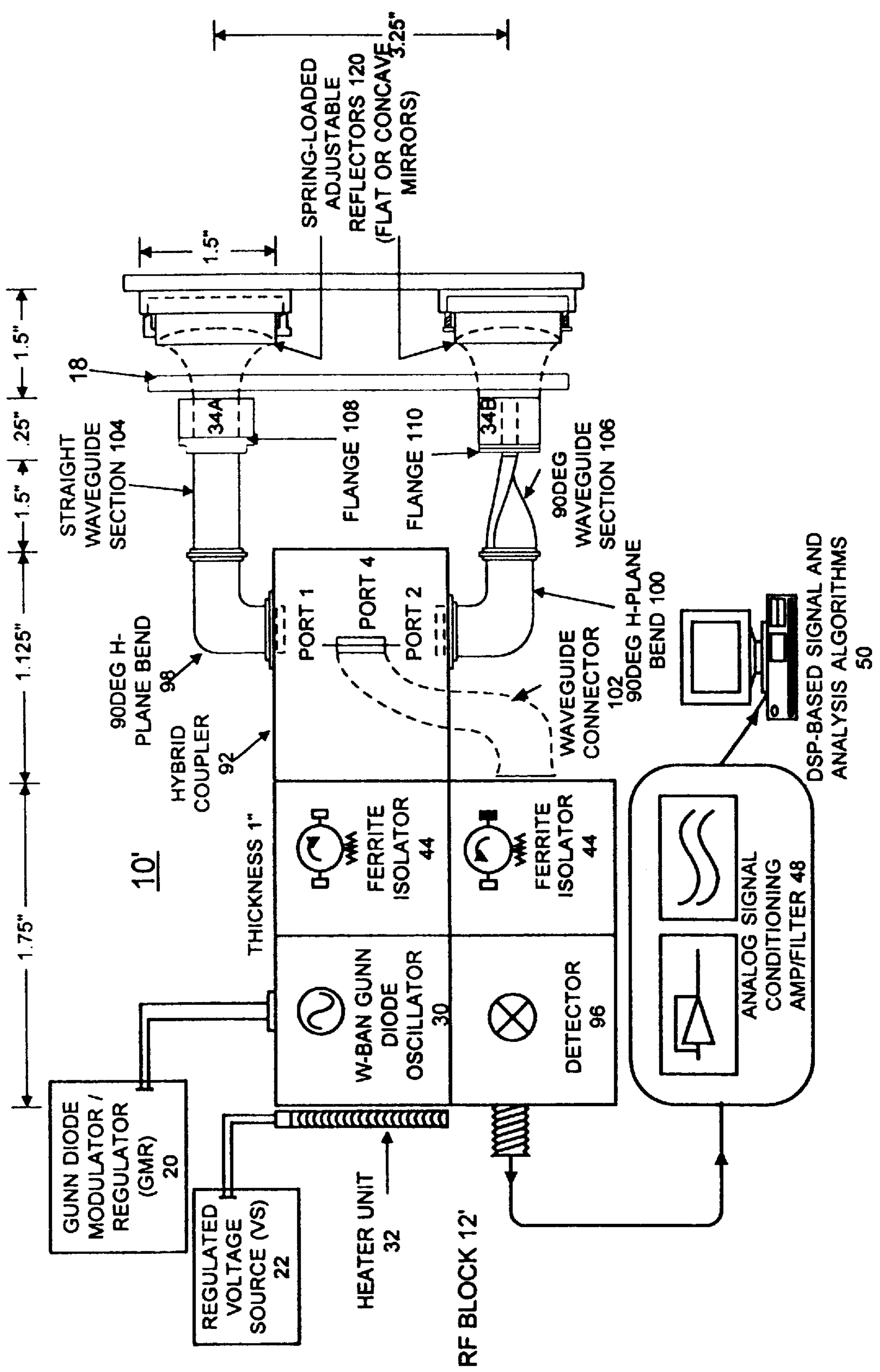
FIG. 6 is a schematic and block diagram representation of an alternative millimeter wave sensor for on-line inspection of thin sheet dielectrics, particularly fabric materials, in accordance with the present invention.

Referring now to FIG. 6, there is shown a simplified schematic and block diagram representation of an alternative MMW system 10', particularly for fabric materials, with an alternative sensor 12'. The same reference characters as used in FIGS. 1A, 1B, and 1C are used for similar or unchanged components. The millimeter wave sensor 12' is a focused-beam, cross-polarized, differential sensor configuration. The millimeter wave sensor 12 of FIG. 1 uses a single antenna 34 and reflector 16, with the material 18 to be tested in between them. In system 10, the single antenna 34 is used to transmit and receive the monitored millimeter wave signals. Using the quadrature IF detector 46, the sensor 12 measures the amplitude and phase changes of the received signal with respect to the transmitted signal. For thin materials like fabric, it has been demonstrated by imaging or testing several fabric samples in the laboratory that the phase is more sensitive than the amplitude.

An alternative, differential sensing system 10' was designed as shown in FIG. 6. Instead of a single antenna and reflector arrangement in the original system 10, a dual arrangement of pair antennas 34A and 34B and corresponding dual reflectors 16' is provided in the alternative, differential sensing system 10'. The separation between the two sensing locations is provided such that there is no coupling or interference between the two signals of antennas 34A and 34B. Because of close proximity, for example, about 3 inches, vibrational signal levels are expected to be identical at the two locations. Consequently, if a difference of the two sensor signals is obtained, it is possible to subtract out the vibrational signals or noise. If, on the other hand, a defect lies in the field of view of one sensor and not the other, the differencing scheme will bring out the defect related signal. More importantly, the fabric background is subtracted out, enhancing the contrast of the defect signal.

A hybrid coupler 92, also called magic tee, is used to transmit and receive the signals to and from the dual sensor system 10'. The hybrid tee 92 allows splitting of the transmitter power from the GDO 30 into equal parts with identical amplitude and phase in ports 1 and 2. Measurement of the power from port 3 by a differential detector 96 will give the difference of the reflected signals from ports 1 and 2. A first ferrite isolator 44 is used between the GDO 30 and the input of the hybrid coupler 92 to block the back-propagating signal from port 4 which otherwise will interfere with the GDO's performance. A second ferrite isolator 44 is used between the output port 3 of the hybrid coupler 92 and the differential detector 96.

Another novel feature used in the sensor 12' is the use of cross polarized antennas 34A and 34B. A 90 degree 2 waveguide section 106 is used in one arm with the antenna 34B, thereby changing its polarization by 90 degrees with respect to the other arm for antenna 34A. The two antennas 34A and 34B are oriented in such a way that one is sensitive to vertically oriented defects such as warp defects and the other is sensitive to horizontally oriented defects such as pick defects. As a result, even if the same defect lies in the field of view of both antennas, the differential sensing would still give defect related signal because one sensor will be more sensitive than the other depending the defect orientation. The sensor 12' was tested successfully on the loom. Vibrational noise was subtracted out very effectively. At the same time, different defects introduced during weaving were detected and imaged very well.

Figure 7B:
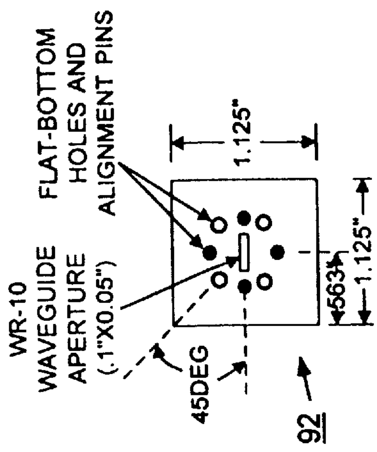
FIG. 7B is a schematic diagram representation illustrating a front view and overall dimensions of the block type millimeter wave hybrid coupler of FIG. 6.
Figure 7D:
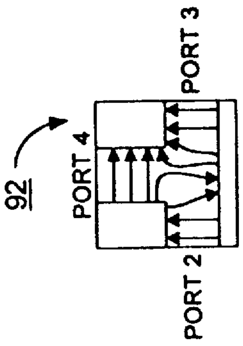
FIG. 7D is a schematic diagram representation illustrating an E-plane view of the electric field distribution for wave incident in port 4 of the block type millimeter wave hybrid coupler of FIG. 6.
Figure 7A:
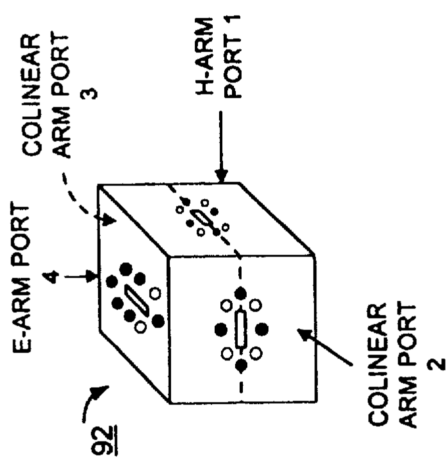
FIG. 7A is a schematic diagram representation illustrating a port configuration for a block type millimeter wave hybrid coupler of FIG. 6.
Figure 7C:
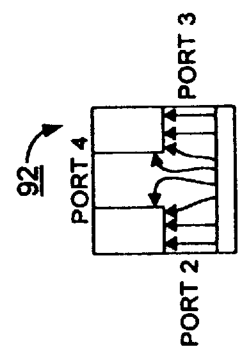
FIG. 7C is a schematic diagram representation illustrating an E-plane view of the electric field distribution for wave incident in port 1 of the block type millimeter wave hybrid coupler of FIG. 6.

FIGS. 7A, 7B, 7C, and 7D show different perspectives of the block type hybrid coupler 92 which acts both as an in phase power divider and an out of phase (180°) power combiner. The two halves of the block type compact hybrid coupler 92 are shown with dashed line in FIG. 7A that are constructed using high conductivity coated plates and using electrodeposition technique. The basic operation of this hybrid coupler 92 is illustrated in FIGS. 7C and 7D in which the intrinsic E-plane view and H-plane symmetry of the device allows for equal (3 dB) in phase and out of phase splitting of the energy. With port 4 (E-arm) matched, the dominant mode ($TE_{10}$) MMW signal from port 1 (H-arm) couples in-phase into ports 2 and 3 due to H-plane symmetry. On the other hand, with port 1 matched, the signal from port 4 couples out of phase into ports 2 and 3 due to E-plane symmetry of the junction. This property of the hybrid coupler 92 is used to measure sum and difference signals (ports 1 and 4) by precise matching of transmission and reflection paths. Unlike standard magic-tee couplers in which intrinsic symmetry of the device is the only factor for port isolation, the block type hybrid coupler 92 used in system 10' uses matched loading at each port which makes it a narrow-band (covering =60% of the bandwidth) device that is specifically designed to provide exceptionally low return loss (<23 dB), high port-to-port isolation (>23 dB for collinear arms), and minimum insertion loss(<0.3 dB). As a result, the hybrid coupler 92 is particularly useful for precise power dividing and combining applications.

Having reference to FIG. 7A for differential sensor configuration 12', the millimeter wave block-type waveguide detector 96 is used at port 4. The detector 96 is a silicon beam-lead diode which operates at square-law region and has 3.0: 1.0 maximum VSWR, ±2 dB flatness, and a minimum sensitivity of 200 mV/mW. As described above, with two sinusoidal signals going through equal path lengths and incident on ports 2 and 3 ($S_2$) and ($S_3$) of the hybrid coupler 92 shown in FIGS. 7A, 7B, 7C, and 7*d*, the waves will couple 180° out of phase into port 4 (E-arm) which can be represented as:

$$S_2=A_2 \cos(\omega_{RF}t+\phi_2) \quad (6)$$

$$S_3=A_3 \cos(\omega_{RF}t+\phi_3+\pi)-A_3 \cos(\omega_{RF}t+\phi_3) \quad (7)$$

The above two signals having the same frequency simultaneously appear at the diode junction. With the diode operating in square-law region, 3-term small signal approximation for voltage-current (V-I) diode characteristics can be written as $$I(v)=I_O+vG_d+(v^2/2)\alpha G_d \quad (8)$$

$$\text{where } \alpha=q/nkT \quad (9)$$

with $I_0$ being the bias current (this term vanishes for zero-biased detectors), v is the small AC signal, $G_d$ is the diode dynamic conductance, q is the electron charge, k is Boltzman's constant, T is temperature , and n is the ideality factor which is dependent on the diode structure and varies from 1.2 to 2.0 for Schottky barrier diodes to about 2.0 for point-contact silicon diodes used for detector 96. In the square-law region, the diode output can be approximated from the third term in (8) which once bandpass filtered can be approximated as $$S_4 \propto A \cos(\phi_1+\phi_2) \quad (10)$$

which represents a rectified DC output of amplitude A ($\propto A_1A_2$) and phase ($\phi_1+\phi_2$) that is proportional to the difference between millimeter wave signals $S_2$ and $S_3$.

Figure 8B:
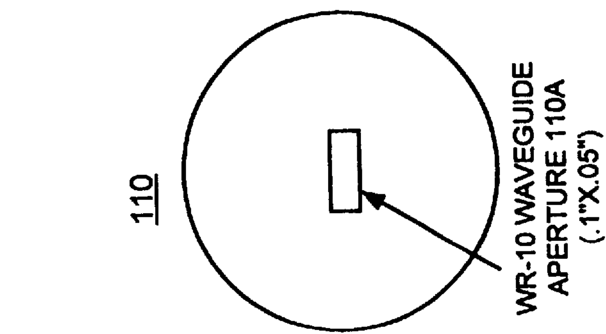
FIGS. 8A and 8B togther provide a schematic diagram representation illustrating a front view of a pair of cross-polarized electroformed high conductivity silver deposited flange mountings for the block type millimeter wave hybrid coupler of FIG. 6.
Figure 8A:
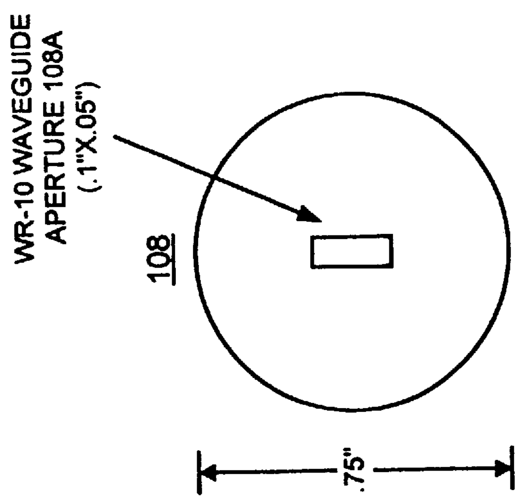
Figure 10:
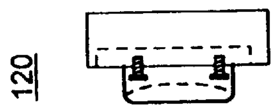
FIG. 10 is a schematic diagram representation illustrating a side view of the pair of optically polished aluminum reflectors of FIG. 9.
Figure 9:
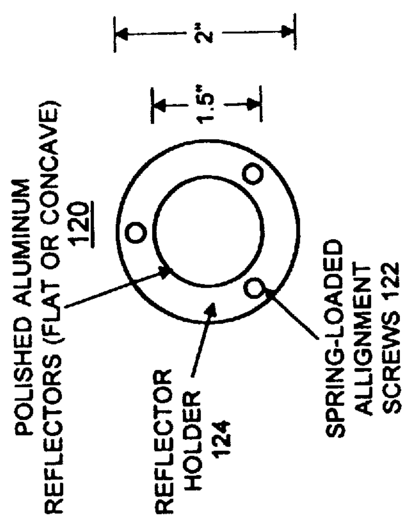
FIG. 9 is a schematic diagram representation illustrating a front view of a pair of optically polished aluminum reflectors with three spring-loaded alignment screws.

Referring to FIG. 8A and 8B there is shown a front view of the two flange-mounted arms 108 and 110 of the differential sensor configuration 12' of FIG. 6. FIGS. 9 and 10 shows front and side view of the reflector mirrors marked as 120 in FIG. 7. Both flat and concave mirror structures can be used in different applications. The concave mirror is designed to have focal length to focal depth ratio of one (F/D=1). A pair of WR-10 flange apertures 108A, 110A shown in FIG. 8 are oriented 90° with respect to each other. This cross-polarized configuration of the antennas serves both to discriminate preferred orientation of sample inhomogeneities and to terminate any cross-coupling between the two differential arms. When the same reflected signal from the test material is incident at both arms, no net change is detected by the sensor 12'. Also, with the electric field distribution at the two apertures 108A, 110A being perpendicular to each other, the reflected radiation does not couple to the other arm, providing perfect isolation of the two arms. Only mismatch between the two arms introduced by changes in the dielectric material 18' under test results in a net signal.

To increase returned power from the sample 18' and to further isolate the cross-polarized arms, a focused beam reflector configuration was also tested. It should be noted that, in all cases examined, cross-coupling between the two sensing arms was never detected in differential sensing mode due to multiple wavelength separation of the two arms. A concave reflector mirror 120 was also constructed and used in some test cases. Using Gaussian optic design, the concave mirrors with spring-loaded adjusting screws 122 were made to give a F/D ratio of one. This structure resulted in focusing of the reflected beam to a small area centered at the waveguide aperture. The problem of cross-coupling between closely spaced antennas is also wavelength dependent, $\theta_3$dB $\approx(70\lambda/D)°$ with D representing the largest antenna dimension and $\lambda$ the operating wavelength. It is noted that millimeter wave radiating structures intrinsically offer much higher isolation in comparison to their microwave counterparts.

Figure 11:
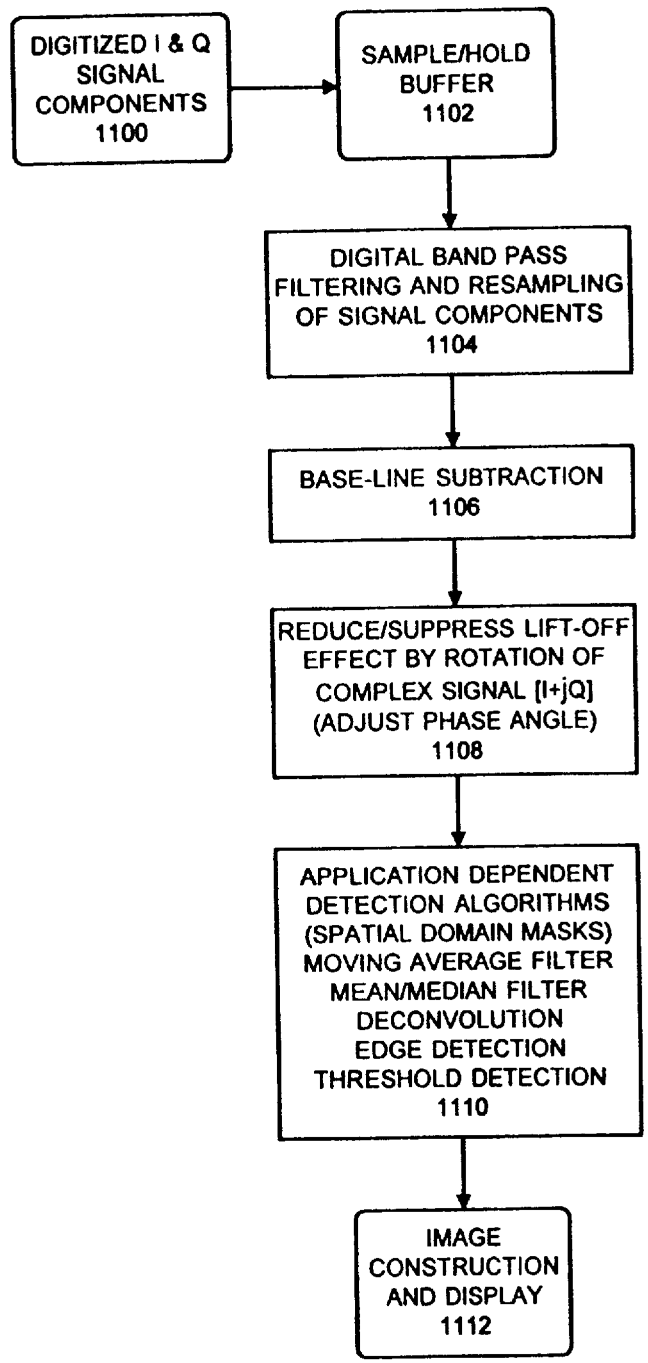
FIG. 11 is a flow chart illustrating sequential steps performed for on-line inspection of thin sheet dielectrics by the millimeter wave sensor of FIGS. 1A and 1B in accordance with the present invention.

FIG. 11 shows a simplified flow diagram of the DSP-based data acquisition and processing section 50 following the analog conditioning stage 48 depicted in FIGS. 1B and 6. The software algorithms used for signal detection and enhancement are application dependent and can be conveniently modified through software implementation. The general steps consists of digitization of the acquired analog data 1100, sample and hold buffering 1102, pre-filtering 1104, baseline subtraction at block 1106, signal rotation 1108, detection 1110, and ultimately image construction 1112, as shown in FIG. 11. To reduce/suppress the effect of possible signal modulation due to variation of liftoff distance between the antenna and test specimen in absolute mode configuration and to better isolate background variations, a novel software-based algorithm utilizes rotation of phase-quadrature signal components to adjust the initial phase angle so as to minimize lift-off phase angle, as indicated at block 1110. Rotation of the complex signal allows isolation of lift-off phase from one channel that consequently leads to improved detection. Other software-based frequency and spatial domain algorithms discussed with respect to FIGS. 1A, 1B, 1C and 2 for signal detection and enhancement such as moving average filter, mean/median filter, deconvolution, edge detection, and threshold detection are application dependent and can be conveniently modified through the software at block 1110.

While the present invention has been described with reference to the details of the embodiments of the invention shown in the drawing, these details are not intended to limit the scope of the invention as claimed in the appended claims.

What is claimed is:

1. A millimeter wave sensor for non-destructive inspection of thin sheet dielectric materials comprising:

source oscillator means for generating a millimeter wave electromagnetic energy signal; said millimeter wave electromagnetic energy signal having a single frequency above 30 GHz;

heater means coupled to said oscillator means for minimizing temperature variations and stabilizing said source oscillator means;

antenna means coupled to said source oscillator means for transmitting said millimeter wave electromagnetic energy signal to a sample thin sheel dielectric material and for receiving a reflected millimeter wave electromagnetic energy signal from the sample thin sheel dielectric material;

separating means coupled between said source oscillator means and said antenna means for separating said millimeter wave electromagnetic energy signal into transmitted and received electromagnetic energy signal components; and detecting means for detecting change in both amplitude and phase of said transmitted and received electromagnetic energy signal components.

2. A millimeter wave sensor as recited in claim 1 wherein said source oscillator means is a Gunn diode oscillator.

3. A millimeter wave sensor as recited in claim 2 wherein said Gunn diode oscillator is mounted on said heater means for maintaining said single frequency of said millimeter wave electromagnetic energy signal.

4. A millimeter wave sensor as recited in claim 2 wherein said single frequency of said millimeter wave electromagnetic energy signal is selectively provided in a range between 75 GHz and 110 GHz.

5. A millimeter wave sensor as recited in claim 2 wherein said single frequency of said millimeter wave electromagnetic energy signal is selectively provided for the sample material.

6. A millimeter wave sensor as recited in claim 1 wherein said antenna means is a small millimeter wave antenna.

7. A millimeter wave sensor as recited in claim 1 wherein said antenna means is selectively provided for the sample material.

8. A millimeter wave sensor as recited in claim 1 wherein said antenna means is an open-ended waveguide antenna.

9. A millimeter wave sensor as recited in claim 1 wherein said antenna means is a standard gain pyramidal horn antenna.

10. A millimeter wave sensor as recited in claim 1 wherein said antenna means is corrugated scalar horn antenna.

11. A millimeter wave sensor as recited in claim 1 wherein each of said source oscillator means, heater means, antenna means, separating means and detecting means is a block type, microstrip component.

12. A millimeter wave sensor as recited in claim 1 wherein said separating means include a ferrite circulator isolator.

13. A millimeter wave sensor as recited in claim 1 wherein said detecting means include quadrature IF mixer (QIFM).

14. A millimeter wave sensor for non-destructive inspection of thin sheet dielectric materials comprising:

a source oscillator for generating a millimeter wave electromagnetic energy signal; said millimeter wave electromagnetic energy signal having a single frequency above 30 MHz;

a pair of cross polarized antennas for transmitting said millimeter wave electromagnetic energy signal to a sample thin sheel dielectric material and for receiving a reflected millimeter wave electromagnetic energy signal from the sample thin sheel dielectric material;

separating means coupled between said source oscillator and said pair of cross polarized antennas for separating said millimeter wave electromagnetic energy signal into transmitted and received electromagnetic energy signal components, said separating means including an isolator and a hybrid tee, said isolator coupled to said source oscillator and said hybrid tee coupled between said isolator and said pair of cross polarized antennas and said hybrid tee separating said millimeter wave electromagnetic energy signal into transmitted and received electromagnetic energy signal components; and differential detecting means coupled to said hybrid tee for detecting a difference of the reflected signals of said pair of cross polarized antennas.

* * * * *